(12) United States Patent
Imamura et al.

(10) Patent No.: US 7,544,658 B2
(45) Date of Patent: Jun. 9, 2009

(54) ROTARY MOTOR MOLECULE $V_1$-ATPASE

(75) Inventors: Hiromi Imamura, Kanagawa (JP);
Masasuke Yoshida, Kanagawa (JP);
Ken Yokoyama, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 537 days.

(21) Appl. No.: 10/535,667

(22) PCT Filed: Oct. 9, 2003

(86) PCT No.: PCT/JP03/12982

§ 371 (c)(1),
(2), (4) Date: Aug. 8, 2005

(87) PCT Pub. No.: WO2004/046350

PCT Pub. Date: Jun. 3, 2004

(65) Prior Publication Data

US 2008/0064078 A1 Mar. 13, 2008

(30) Foreign Application Priority Data

Nov. 20, 2002 (JP) ............................. 2002-337212

(51) Int. Cl.
*A61K 38/16* (2006.01)
(52) U.S. Cl. .................... 514/12; 530/300; 530/324; 424/94.5
(58) Field of Classification Search .............. None
See application file for complete search history.

(56) References Cited

OTHER PUBLICATIONS

Imamura, et al., 2003, PNAS, 100, 2312-2315.*
Xiong, 1995, The Journal of biological chemistry, 270, 23300-23304.*
Yokoyama, 2000, The Journal of biological chemistry, 275, 13955-13961.*
Soong, 2000, Science, 290, 1555-1558.*
K. Yokoyama et al., "*Thermus thermophilus* membrane-associated ATPase, Indication of a eubacterial V-type ATPase", J. Biol. Chem., vol. 265, No. 35, pp. 21946-21950, 1990.
K. Yokoyama et al., "Isolation of prokaryotc $V_0V_1$-ATPase from a thermophilic edubacterium *Thermus thermophilus*", J. Biol. Chem., vol. 269, No. 16, pp. 12248-12253, 1994.
K. Yokoyama et al., "V-ATPase of *Thermus thermo philus* is inactivated during ATP hydrolysis but can synthesize ATP", J. Biol. Chem., vol. 273, No. 32, pp. 20504-20510, 1998.
K. Yokoyama et al., "V-Type $H^+$-ATPase/synthase from a thermophilic eubacterium, *Thermus thermo philus*. Subunit structure and operon", J. Biol. Chem., vol. 275, No. 18, pp. 13955-13961, 2000.
Y. Kato-Yamada et al., "Direct observation of the rotation of ε subunit in $F_1$-ATPase", J. Biol. Chem., vol. 273, No. 31, pp. 19375-19377, 1998.
H. Noji et al., "Direct observation of the rotation of $F_1$-ATPase", Nature, vol. 386, No. 6622, pp. 299-302, 1997.
H. Imamura et al., "Evidence for rotation of $V_1$-ATPase", Proc. Natl. Acad. Sci. U.S.A., vol. 100, No. 5, pp. 2312-2315, Mar. 2003.
K. Yokoyama et al., "Rotation of the proteolipid ring in the V-ATPase", J. Biol. Chem., vol. 278, No. 27, pp. 24255-24258, Jul. 4, 2003.

* cited by examiner

*Primary Examiner*—Andrew D Kosar
*Assistant Examiner*—Satyanarayana R Gudibande
(74) *Attorney, Agent, or Firm*—Wenderoth, Lind & Ponack, L.L.P.

(57) ABSTRACT

A complex rotating in the presence of ATP, which has three A subunits, three B subunits and one D subunit constituting the $V_1$ portion of a $V_0V_1$-ATPase.

12 Claims, 4 Drawing Sheets

ROTARY MOTOR MOLECULE V₁-ATPASE

This application is a U.S. national stage of International Application No. PCT/JP2003/012982 filed Oct. 9, 2003.

TECHNICAL FIELD

The present invention relates to a novel rotary motor molecule $V_1$-ATPase useful for a nanoactuator of a micromachine or a nanomachine, or the like.

BACKGROUND ART

Attention is being given to the development of a micromachine or a nanomachine that mechanically moves according to the size of a molecule. This is because such micromachine or nanomachine is considered useful for, e.g., a molecule robot that lays out the wiring of a molecule computer or a medical robot that works a cure in the body.

For the fabrication of a micromachine and a nanomachine, development of a variety of technologies is required, including individual element devices (a sensor, an actuator and a miniature machine) to processes of assembling them (micromachining and nanomaching). In particular, the development of microactuators and nanoactuators (rotary motors), i.e., micromachine drive devices, is essential for self-regulating movement of machines, and the development of motor devices utilizing diverse precise handling technologies is being pursued. However, even microactuators made by processes to which precise handling technologies are applied are no smaller than about 100 μm. Further miniaturization of motor apparatuses is being required to install them in micromachines and nanomachines.

Thus, aside from construction of a motor by precise handling technology, utilization of a single molecule having rotary movement capability as a motor is proposed.

In general, a molecule capable of being a motor needs to satisfy two factors: having a power mechanism that converts outer energy into rotary movement, and achieving rotation in one direction. Low molecular organic compounds satisfying such conditions that are known include, for example, (3R, 3'R)-(P,P)-trans-1,1',2,2',3,3',4,4'-octahydro-3,3'-dimethyl-4,4'-bipheanthrydiene (Nature 401: 152-155, 1999) and Triptycyl(4)helicene (Nature 401: 150-152, 1999). The former has symmetry to the right and to the left of the carbon-carbon double bond, but has a twisted structure due to steric interlocking. Addition of suitable heat or light thereto makes it possible to rotate the molecule in one direction through four process steps. Also, one cycle is completed through two light reactions and a heat isomerization, with the movement proceeding in one direction only. In other words, this organic compound conducts rotary motion via heat isomerization and light reaction. Rotation via light reaction is very rapid (a level of picoseconds), but rotation via heat isomerization needs a few minutes, and so is unsuitable for actual use. Furthermore, the compound poses the problem that the driving force of rotation is extremely weak. On the other hand, the heat isomerization causes one-direction rotation of the molecule utilizing the chemical reactions of phosgene addition and the formation and cleavage of urethane bonding. However, this molecule is incapable of repeating rotation, a fatal defect for an actuator.

On the other hand, as a single molecule motor capable of being utilized in a micromachine, a nanomachine or the like, biomolecules are known that include a flagellum motor (Microbiol. 6: 1-18, 1967, Nature 245: 380-382, 1973), an ATP synthase (Nature 386: 299-302, 1997), a myosin motor (Biochem. Biophys. Res. Comm. 199: 1057-1063, 1994, Curr. Opin. Cell Biol. 7: 89-93, 1995), a microtubule-based motor (Cell 42: 39-50, 1985), a motor protein of nucleic acid synthase (Nature 409: 113-119, 2001, and the like.

Of these, an ATP synthase is a membrane protein present ubiquitous, at such locations as the inner membranes of mitochondria in eukaryotes, thylakoid membranes of chloroplasts, a prokaryote cell membrane, and the like, and synthesizes most ATP consumed in cells. An ATP synthase ($F_0F_1$-ATP synthase) is a huge membrane protein complex with molecular weight up to about 500 thousand, and consists of an $F_0$ portion present inside a membrane and an $F_1$ portion present outside the membrane. The $F_0$ portion is a passage for a proton ($H^+$) to pass through the membrane, and the $F_1$ portion is a catalyst portion that synthesizes and hydrolyzes ATP. The molecular weight of the $F_1$ portion is about 380 thousand, for example, the subunit composition of the $F_1$ portion in an ATP synthase derived from bacteria is $\alpha_3\beta_3\delta\gamma_1\epsilon_1$. $\alpha$ and $\beta$ subunits both have a similar ATP binding portion, but catalyst activity is present in the $\beta$ subunit. Both alternately align to form a ring and in the center of this $\alpha_3\beta_3$ ring, a $\gamma$ subunit is present. A $\delta$ subunit binds to the top of the $\alpha_3\beta_3$ ring; an $\epsilon$ subunit that controls ATP hydrolysis activity binds to the $\gamma$ subunit. On the other hand, the $F_0$ portion has a molecular weight of about 100 thousands, and the amino acid composition contains in quantity glutamic acid and asparaginic acid, necessary for proton movement. The subunit composition is $a_1b_2c_{9-12}$, "c" subunits are arranged like a ring (the "c" ring) in the membrane, and to the "c" ring are bound subunit "a" and two "b" subunits each having an arm protruding far outside the membrane. Hence, an $F_0F_1$-ATP synthase has an $F_1$ portion and an $F_0$ portion which are bound to each other at two sites: $\gamma\epsilon$-"c" ring and $\delta b_2$. A further characteristic is the fact that this $F_0F_1$-ATP synthase molecule has two kinds of torque generating devices. One is an ATP driving type device present in the $F_1$ portion and the other is a proton driving type device present in the $F_0$ portion. That is, when the $F_0$ portion takes a proton in the cell membrane, the "c" ring rotates clockwise; when the $F_0$ portion discharges a proton to the outside of the cell membrane, the "c" ring rotates anticlockwise. On the other hand, during ATP synthesis, the F, portion rotates clockwise viewing the $\gamma$ subunit from the $F_0$ side, and the $F_1$ portion rotates anticlockwise during ATP decomposition. By providing these two kinds of torque generating devices, the torque generated by ATP synthase is on the order of tens of piconewton·nm, and thus the synthase has a sufficient driving force for a molecule motor. Additionally, an ATP synthase acts in a water system and so it is most suitable as an actuator working in the body, and also can manipulate a protein, sugar, a lipid, or a nucleic acid in the body because it has sufficient power for moving actin.

The inventors of the present invention improved this $F_1F_1$-ATP synthase molecule, and have already invented and filed the invention of a modified $F_0F_1$-ATP synthase molecule capable of controlling over a wide rotation speed range and its utilization (Japanese Patent Application No. 2002-148232; filing date: May 22, 2002). In addition, recently, reported was a rotary motor molecule, which is made by incorporating a zinc binding site into an $F_1$-ATP synthase molecule and which is capable of controlling the initiation and stop of the rotation by means of the zinc (Nature Materials 1: 173-177, 2002).

As described above, various rotary motor molecules are proposed as driving members of a micromachine, a nanomachine, and the like, and the molecules each have characteristics regarding type of rotation, the revolution number, torque, the method of controlling rotation, etc. Accordingly, for actual fabrication of a micromachine or a nanomachine, an appropriate molecule needs to be selected from a variety of candidate molecules depending on its application and machine construction. However, it cannot be said that the rotary motor molecules reported thus far can each be suitable for all the different applications and constructions of a micromachine and a nanomachine. For this reason, upon the development of a micromachine or a nanomachine or the like, each addition of one more to the lineup of rotary motor molecules is greatly desired.

Thus, this application is intended to provide a novel rotary motor molecule that is different in properties from the conventional rotary motor molecules.

In addition, the application also has another subject of providing an improved, novel rotary motor molecule which further smoothens the rotary motion and also adds a means for the molecule to transfer the rotary motion.

DISCLOSURE OF INVENTION

This application, as the invention for solving the above-described problem, provides a rotary motor molecule $V_1$-ATPase rotating in the presence of ATP, which is a complex molecule having three A subunits, three B subunits and one D subunit constituting the $V_1$, portion of a $V_0V_1$-ATPase.

The $V_1$-ATPase of this invention includes the A subunit as a catalyst portion, A and B subunits are arranged alternately, and from a hexamer cylinder like the $\alpha_3\beta_3$ of a $V_0V_1$-ATPase. The D subunit is embedded in the central cavity of this $A_3B_3$ cylinder, an F subunit is bound to the D subunit, and the D and F subunits act as a rotor (rotary shaft, rotary axis).

In one mode of this invention, the rotary motor molecule $V_1$-ATPase is heat resistant, and in this case it is preferred that the $V_1$-ATPase is derived from the thermophile bacteria, *Thremus thermophilus*.

Further, the rotary motor molecule $V_1$-ATPase derived from the thermophile, *Thremus thermophilus* is a complex having three peptides of SEQ ID NO:3 corresponding to the A subunit, three peptides of SEQ ID NO:4 corresponding to the B subunit, and one peptide of SEQ ID NO:5 corresponding to the D subunit is one preferred mode.

Furthermore, in another mode of the invention, the rotary motor molecule $V_1$-ATPase of the present invention is an improved type molecule which has at least one substitution of Ala residue for the 232nd Ser residue and Ser residue for the 235th Thr residue in SEQ ID NO:3.

In this improved $V_1$-ATPase, the improvement of the A subunit, the catalyst portion, allows dissolution of MgADP inhibition and acceleration of ATP hydrolysis activity. Rotation of a wild type of $V_1$-ATPase tends to be suppressed due to MgADP inhibition, and the modified $V_1$-ATPase that prevents MgADP inhibition exhibits efficient rotational motion.

Furthermore, a further mode of the present invention is that the rotary motor molecule $V_1$-ATPase is an improved molecule in which one or both of the A and B subunits is fixed on a substrate. In this case, a preferred mode is that the molecule is fixed on the substrate via an His tag bound to the N terminal of the A subunit.

In a still another mode of the invention, the rotary motor molecule $V_1$-ATPase has a joint bound to the D subunit. In this case, the joint material is bound to at least one of Cys residue substituted for the 48th Glu residue and Cys residue substituted for the 55th Gln residue in SEQ ID NO:5, and the case where all the Cys residues in the A and B subunits are replaced by non-Cys residues is another preferred mode.

That is, the rotary motor molecule $V_1$-ATPase of the present invention comprises the $V_1$ portion (a complex comprised of three A subunits, three B subunits, one D subunit) of V type (tonoplast type) ATPase ($V_0V_1$-ATPase) present in organelles (vacuole, lysosome, Golgi vesicle, cell membrane, coated vesicle, secretory granule, etc) of a bacterium or a eukaryote. Although a $V_0V_1$-ATPase synthase has already known to serve as a rotary motor molecule, the $V_1$ portion ($V_1$-ATPase) of this $V_0V_1$-ATPase was not known to have rotational motion at all. The $V_1$-ATPase of this invention has been completed by for the first time finding that the D subunit located inside a "cylindrical body" comprised of three A subunits and three B subunits a D subunit functions as a rotary shaft.

In addition, the $V_1$ portion of a $V_0V_1$-ATPase has one F subunit bound to the D subunit, but the $V_1$-ATPase of this invention also includes a molecule that binds this F subunit. Also, examples of $V_1$-ATPases of this invention include not only a wild type, but also a variety of variants as described above. Furthermore, the examples include a variant into which a zinc recognizing portion is incorporated, as disclosed in Nature Materials 1: 173-177, 2002 as noted above.

Hereinafter, each invention as described above will be set forth in detail with embodiments of the invention. For the embodiments, a variety of arts used in order to carry out this invention, exclusive of the arts particularly indicating the sources thereof, can be readily and surely carried out by a person skilled in the art in accordance with literatures or the like. For instance, descriptions of genetic engineering and molecular biological technology, such as Sambrook and Maniatis, in Molecular Cloning-A Laboratory Manual, Cold Spring Harbor Laboratory Press, New York, 1989; and Ausubel, F. M. et al., Current John Wiley & Sons, New York, N.Y. Protocols in Molecular Biology, 1995 can be used for reference.

BEST MODE FOR CARRYING OUT THE INVENTION

The rotary motor molecule $V_1$-ATPase of this invention is the $V_1$, ($V_1$-ATPase) portion of $V_0V_1$-ATPase produced from various bacteria or eukaryotes. The $V_1$-ATPase can be produced by genetic engineering using a polynucleotide (DNA fragment, RNA fragment, or preferably cDNA fragment. Hereinafter, it may be denoted as "$V_1$-ATPase polynucleotide") encoding the $V_1$-ATPase. Namely, sequences of the polynucleotide (cDNA fragment) encoding the $V_0V_1$-ATPase are disclosed in many data bases (e.g., GenBank data base: URL: http://www.ncbi.nlm.nih.gov), and using the sequence information in a probe hybridization process or a PCR process, the polynucleotide (cDNA fragment) encoding the $V_0V_1$-ATPase can be readily obtained from existent cDNA libraries, or the like.

Expression of this $V_1$-ATPase polynucleotide using a well-known genetic engineering process can provide a complex $V_1$-ATPase comprised of three A subunits, three B subunits and one D subunit. For instance, the recombination of a $V_1$-ATPase polynucleotide into an expression vector having an RNA polymerase promoter and then addition of this recombinant vector into an in vitro translation system including RNA polymerase corresponding to the promoter, such as rabbit reticlocyte lysate or a wheat embryo extract, can produce the $V_1$-ATPase having rotation capability in vitro. Examples of the RNA polymerase promoter can include T7, T3, and SP6. Examples of vectors containing these RNA polymerase promoters include pKA1, pCDM8, pT3/T7 18, pT7/3 19, and pBluescript II. Also, the expression of a $V_1$-ATPase polynucleotide in a suitable host-vector system can produce the rotary motor molecule $V_1$-ATPase in a prokaryotic cell such as *E. coli.*, or hay bacillus, a eukaryotic cell such as yeast, an insect cell, a mammal cell, or plant cell, or the like. For example, when the $V_1$-ATPase is expressed in a microorganism such as *E. coli.*, the polynucleotide is recombined into an expression vector having an origin replicable in the microorganism, a promoter, a ribosome binding portion, a DNA cloning portion, a terminator and the like, to prepare an expression vector which transforms the host cell. Culturing this transformant can produce the target $V_1$-ATPase molecules from the culture in quantity. Examples of expression vector for *E. coli* include pUC system, pBluescript II, pET expression system, and pGEX expression system. Furthermore, when the polynucleotide is to be expressed in a eukaryotic cell, the polynucleotide is inserted into an expression vector for a eukaryotic cell, the vector having a promoter, a splicing region, poly(A) addition portion and the like, resulting in a recombinant vector. From eukaryotic cells transfected with this vector can be obtained the target $V_1$-ATPase molecules. Examples of the expression vector include pKA1, pCDM8, pSVK3, pMSG, pSVL, pBK-CMV, pBK-RSV, EBV vector, pRS, and pYES2. Eukaryotic cells that can be used include mammal culture cells such as human embryo renal cell line HEK293, monkey renal cell line COS7, Chinese hamster ovarian cell line CHO, or primary culture cells isolated from human organ, and the like. The eukaryotic cells that can be used also include budding yeast, fission yeast, silkworm cells, and Xenopus egg cells. For the expression vector to be transfected into eukaryotic cells, a known method such as electroporation, calcium phosphate method, ribosome method, DEAE dextran method, and the like may be used. For isolation and purification of the $V_1$-ATPase expressed from the transformant cells, well known separation operations can be carried out in combination. Examples of the isolation and purification include treatment with a modifying agent such as urea or with a surfactant, ultrasonic treatment, enzyme digestion, salting out or the solvent precipitation method, dialysis, centrifugation, ultrafiltration, gel filtration, SDS-PAGE, isoelectric focusing electrophoresis, ion exchange chromatography, hydrophobic chromatography, affinity chromatography, reversed phase chromatography, and the like.

Also, the rotary motor molecule $V_1$-ATPase of this invention is preferably a heat resisting molecule for the sake of industrial utilization. Hence, preferably, a $V_1$-ATPase polynucleotide is derived from a bacterium of *Thermus* genus, *Methanococcus* genus, *Sulfolobus* genus, or the like, which grows at 65° C. or more. Further, use of a $V_1$-ATPase polynucleotide derived from the thermophile *Thermus thermophilus*, which is capable of growing even at 70° C. or more is particularly preferable. The $V_1$-ATPase polynucleotide derived from *Thermus thermnophilus* has the base sequence of SEQ ID NO: 1. The $V_1$-ATPase polynucleotide derived from *Thermus thermophilus* encodes a complex of the polypeptide (F subunit) consisting of the amino acid sequence of SEQ ID NO:2, the polypeptide (A subunit) of SEQ ID NO:3, the polypeptide (B subunit) of SEQ ID NO:4, and the polypeptide (D subunit) of SEQ ID NO:5. Therefore, expressing the 334-4196 nt sequence of SEQ ID NO:1 by means of the aforementioned genetic engineering technology can give a heat resisting $V_1$-ATPase comprising of three A subunits, three B subunits and one D subunit. In addition, expressing the 1-4196 nt sequence of SEQ ID NO: 1 can provide a heat resisting $V_1$-ATPase having one F subunit bound to the D subunit thereof.

A still another preferred mode of the rotary motor molecule $V_1$-ATPase of this invention has substitution of Ala residue for the 232nd Ser residue or substitution of Ser residue for the 235th Thr residue, or both, in SEQ ID NO:3, and a particularly preferred mode is the improved molecule having both substitutions (hereinafter, a molecule having both substitutions may be denoted as a "TSSA variant"). In other words, in contrast to a V-ATPase of a eukaryotic cell, the reaction of the $V_1$-ATPase derived from a bacterium such as *T. thermophilus* has a tendency to be interrupted during the metabolic turnover of the catalyst due to the so-called MgADP inhibition (J Biol Chem 273, 20504-20510, 1998). Normally, this ADP restriction appears within 5 minutes after ATP has been added as a substrate, and in about 10 minutes the $V_1$-ATPase stops ATP hydrolysis. Thus, the inventors of this application have prepared some variants and studied the ADP restriction effects. As a result, the inventors have found that the aforementioned TSSA variant continues ATP activity even for one hour after the addition of ATP as a substrate.

Still another preferred mode of the rotary motor molecule $V_1$-ATPase of this invention is a modified molecule where either the A or B subunit or both is fixed on a substrate. The reason is that this fixation makes it possible to efficiently transmit the rotation of the D subunit. Binding of A and/or B subunit like this on a substrate can be carried out by a variety of methods, for example using covalent bonding, but preferably a method is employed involving bonding His (hectahistidine) tag to the N terminal of A subunit and then bonding this His tag to Ni-NTA slide (Nature 386: 299-302, 1997; FEBS Letters 470: 244-248, 2000).

In another preferred mode of the rotary motor molecule $V_1$-ATPase of this invention, the D subunit is bound to a joint material. The term "joint material" in this case means a material for transmitting the rotational motion of the D subunit of the $V_1$-ATPase to another component (e.g., a gear or a shaft of a motion engine, or the like). Alternatively, this joint material is not for connection to another component, but can also be utilized as a "probe" or a "propeller" for observing the rotation of the $V_1$-ATPase. Examples of joint materials that can be utilized include a plurality of previously mentioned beads (microspheres) that are connected as seen in Embodiments described below, and a fine fiber such as actin filament (Nature 386: 299-302, 1997). This joint material can be bonded to Cys residue of the D subunit, for example, by maleimide or disulfide bonding or the like. However, the D subunit of the $V_1$-ATPase derived from *Thermus thermophilus*, the amino sequence of which was indicated in SEQ ID NO:5, does not have Cys residues, and thus a suitable non-Cys residue needs to be replaced by Cys residue. For this reason, in this invention, a joint material is preferably bound to Cys residue substituted for the 48th Glu residue or Cys residue substituted for the 55th Gln residue (preferably both) in SEQ ID NO:5. In addition, Cys residues other than those in D subunit (a total of nine Cys residues in A subunit, three Cys residues in B subunit) are preferably replaced by other residues (e.g., Ser residues) so that these Cys residues are not bound to the joint material.

Alternatively, a joint material can be made not to bind to D subunit, but to F subunit which binds to D subunit. In this case, for example, the 28th Ser and/or the 35th Ser residue is replaced by Cys residue in the amino acid of SEQ ID NO:2, and to these Cys residues can be bound a joint material.

Furthermore, each of the above-described $V_1$-ATPases can be obtained by replacing a triplet encoding the specified amino residue in a $V_1$-ATPase polynucleotide by means of a method using a mutation kit or the like, the mutagenesis PCR, or a polynucleotide synthesizing method (e.g., Nucleic Acid Res. 25: 3440-3444, 1997), and then expressing this mutated polynucleotide by a genetic engineering process.

Hereinafter, the present invention will be described in terms of Examples in more detail and specifically; however, the invention is by no means limited by the Examples below.

EXAMPLES

1. Material and Method 1-1. Preparation of Proteins

The $V_1$-ATPase was expressed through the use of *E. Coli* BL21-CodonPlus-RP (Stragene) transformed with the plasmid pUCV1 that possessing the DNA sequences encoding each of the A, B, D, and F subunits of the $V_1$-ATPase derived from *T. thermophilus* HB8 under the control of lac promoter. Also, the DNA sequences encoding each of the A, B, D, and F subunits were modified to prepare the following variants (the amino acid positions correspond to SEQ ID NOS:2 to 5).

I: $V_1$-ATPase (A-His8-tags/ΔCys/A-S232A/A-T235S/D-E48C/D-Q55C)
(1) Binding a His tag to the N terminal of the A subunit (A-His8-tags)
(2) Substituting Ser residues for all the Cys residues of the A and B subunits (ΔCys)
(3) Substituting Ala for the 232nd Ser of the A subunit (A-S232A)
(4) Substituting Ser for the 235th Thr of the A subunit (A-T235S)
(5) Substituting Cys for the 48th Glu of the D subunit (D-E48C)
(6) Substituting Cys for the 55th Gln of the D subunit (D-Q55C)

II: $V_1$-ATPase (A-His8-tags/ACys/A-S232A/A-T235S/F-S28C/F-S35C)
(1) Binding a His tag to the N terminal of the A subunit (A-His8-tags)
(2) Substituting Ser residues for all the Cys residues of the A and B subunits (ΔCys)
(3) Substituting Ala for the 232nd Ser of the A subunit (A-S232A)
(4) Substituting Ser for the 235th Thr of the A subunit (A-T235S)
(7) Substituting Cys for the 28th Ser of the F subunit (S28C)
(8) Substituting Cys for the 35th Ser of the F subunit (S35C)

Figure 1:
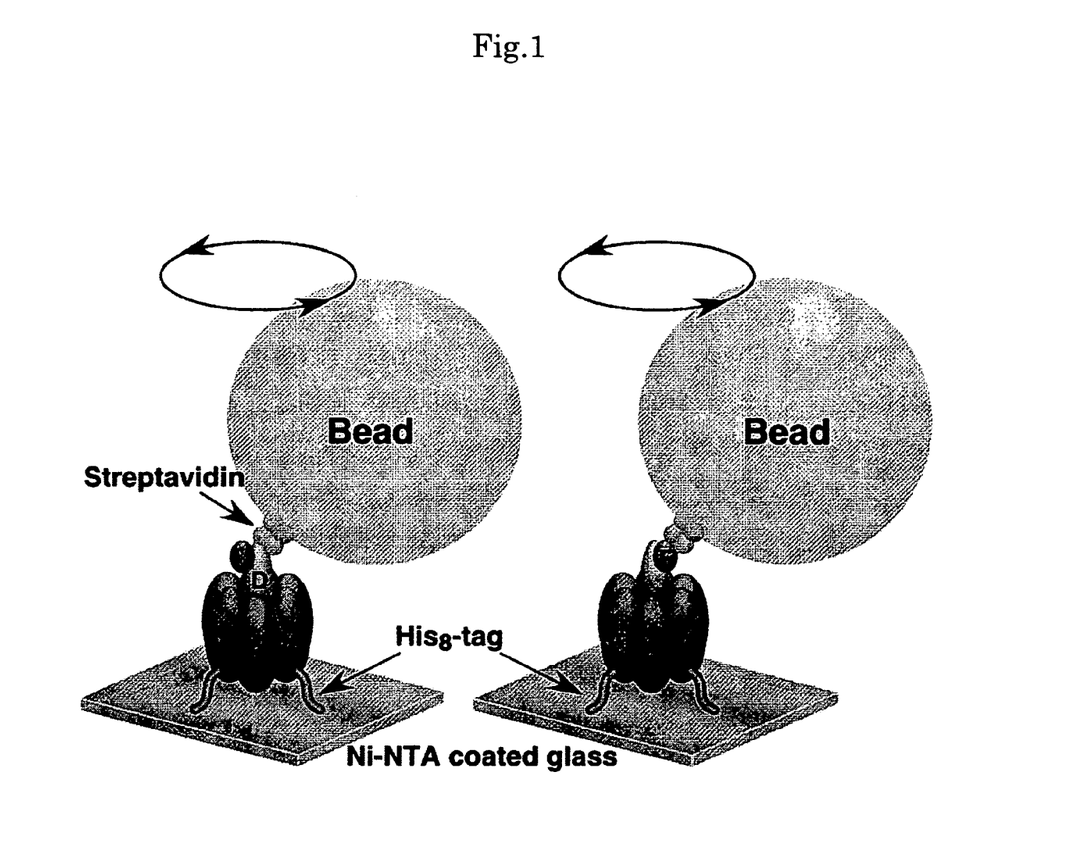
FIG. 1 is a schematic diagram indicating the observed rotation of $V_1$-ATPase. The arrow indicates the direction of rotation.
Figure 2:
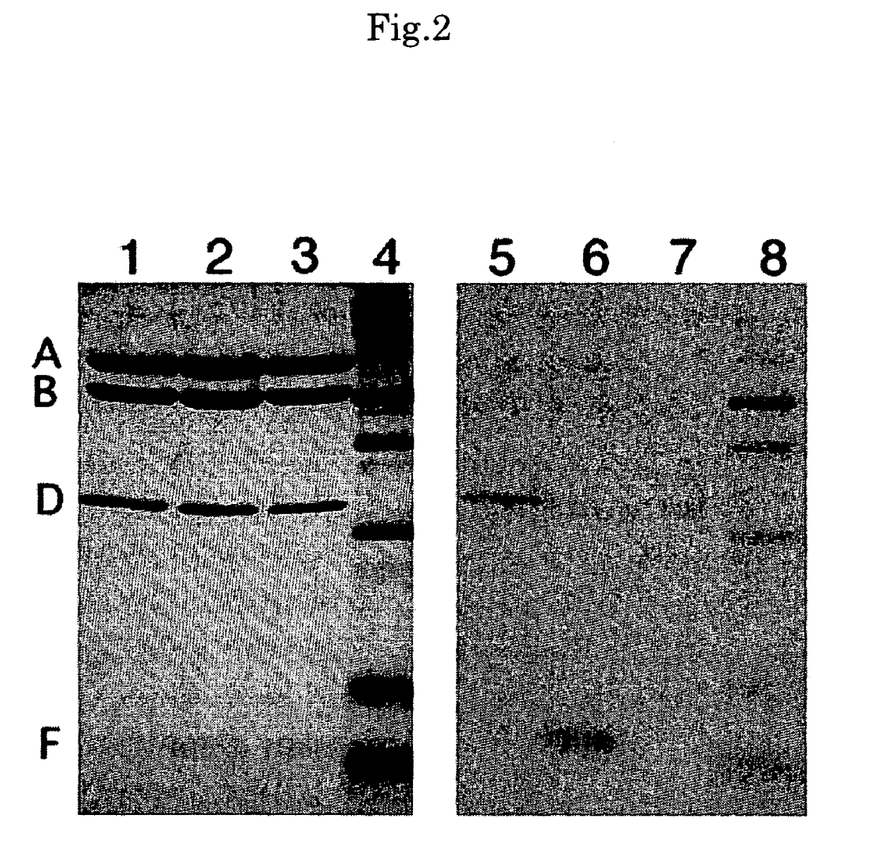
FIG. 2 is the result of western blotting analysis that has confirmed the biotinylation of a D or an F subunit. The left side (lanes 1 to 4) is obtained by CBB staining and the right side (lanes 5 to 8) is obtained by alkaline phosphatase-streptavidine conjugate staining. Lanes 1 and 5 indicate $V_1$-ATPase in which the D subunit was biotinylated, lanes 2 and 6 indicate $V_1$-ATPase with a biotinylated F subunit, lanes 3 and 7 indicate un-biotinylated $V_1$-ATPase, and lanes 4 and 8 indicate molecular-weight markers.

After transformed cells were suspended in 20 mM imidazole/HCl (pH 8.0) containing 0.3 M NaCl, and after the resulting suspension was heated at 65° C. for 30 minutes, the proteins unstable under heat were removed, and then the resulting material was placed into a $Ni^{2+}$-affinity column (Amersham) and eluted with 0.5 M imidazole/HCl (pH 8.0) containing 0.3 M NaCl. To the eluate was added a buffer, and this mixture was given ultrafiltration (VIVA-Spin, VIVA science) and was subsequently put into a RESOURCE Q column. The portion containing a $V_1$-ATPase was placed into Superdex 200 column (Amersham) and there the contamination-relating proteins were removed. The purified $V_1$-ATPase was subjected to biotinylation with more than two moles of 6-[N'-[2-(N-maleimido)ethyl]-N-piperazinylamido]hexyl D-biotinamide (biotin-$PEAC_5$-malaimide, Dojindo). The resulting substance was incubated at 25° C. for 15 minutes and then the protein was placed into a PD-10 Column (Amersham) where the unreacted reagents were removed. Biotinylation of the D and F subunits was confirmed by the western blotting technique using streptavidin-alkalinephosphatase conjugate (Amersham) (FIG. 2).

1-2 Rotation Observation

Flow cell of 5 μl was fabricated from two cover slips (a spacer with a thickness of 50 nm between them). The bottom glass surface was coated with $Ni^{2+}$-nitrilotriacetic acid, and the biotinylated $V_1$-ATPase (0.1-1 μM) contained in the A solution composed of a buffer (50 mM Tris-HCl, pH 8.0, 100 mM KCl, 5 mM $MgCl_2$) and 0.5% (w/v) BSA was poured into the flow cell, and His tags were bound to the glass, thereby fixing the $V_1$-ATPase.

The flow cell was filled with solution of beads (φ=0.56 μm, Bangs Laboratories inc.) coated with 0.1% (w/v) Stereptavidin, binding some beads to the D or F subunit by biotin-streptavidine bonding. The unbound beads were removed by washing.

With the rotation of the $V_1$-ATPase molecule, the rotation of a bead was in ATP of specified concentration (0.2 mg/ml creatine kinase and 2.5 mM creatine phosphate ATP in the regenerating system) observed under a bright field microscope (IX70, Olympus, magnifying power 1000). Also, the state of rotation was recorded with a CCD camera. This $V_1$-ATPase rotation observation system is similar to $F_1$-ATPase rotation system (Proc Natl Acad Sci USA 98, 13649-54, 2001). Specifically, rotation about a slanted bonding, due to the beads being bound to the D or F subunit, was observed (FIG. 2).

1-3. Other Assays

The protein concentrations were determined by UV measurement. The ATP hydrolytic activity was determined from the oxidation of NADH which couples pyruvate kinase and lactate dehydrogenase.

2. Results 2-1. Observation of Rotation

The two variants; the $V_1$-ATPase (A-His8-tags/ΔCys/A-S232A/A-T235S/D-E48C/D-Q55C) and the $V_1$-ATPase (A-His8-tags/ΔCys/A-S232A/A-T235S/F-S28C/F-S35C) were observed for the rotation thereof. The two variants showed kinetics that follow the Michaelis Menten equation, with the two variants having Km of 0.3 to 0.5 mM and Vmax (turnover rate) of about 10 $sec^{-1}$. These values are almost the same as those of the wild type $F_0F_1$-ATP synthase (J Biol Chem 273, 20504-1014, 1998).

2-2. Rotation of D Subunit

When a buffer containing ATP was poured into flow cell, the rotation of a bead bound to D subunit of the $V_1$-ATPase was observed (FIGS. 3A to 3D). In flow cell, rotations of 5 to 10 beads were observed.

The rotation was in one direction, in the case of $F_1$-ATPase the rotation always counterclockwise viewed from the cell membrane side. In a buffer not containing ATP, one-direction rotation distinguishable from Brownian motion was not observed.

Figure 3:
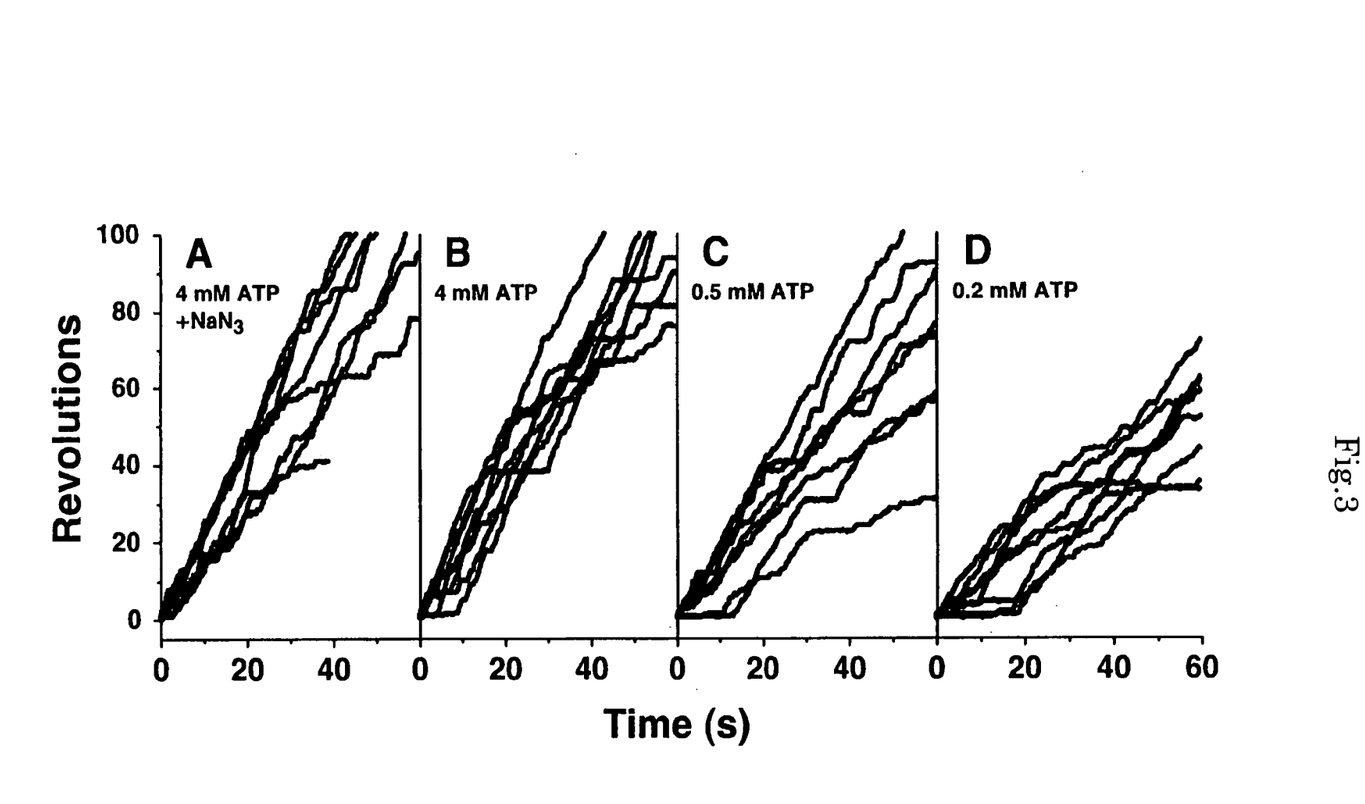
FIG. 3 shows the measurements of rotation of the beads fixed on D subunits over time. "A" shows the rotation of bead in the presence of 4 mM ATP and 0.5 mM sodium azide. "B" to "D" show the results of rotations of beads in the absence of sodium azide, where "B" is 4 mM ATP solution, "C" is 0.5 mM ATP solution, and "D" is 0.2 mM ATP solution.

An azide is known to inhibit both ATPase activity and rotation of the $F_1$-ATPase (Nature 386, 299-302, 1997), but not to inhibit the ATPase activity of a $V_1$-ATPase (J Biol Chem 265, 21946-50, 1990). The rotation of a variant $V_1$-ATPase is the same as the above. This is because an azide did not affect the rotation of a $V_1$-ATPase in the presence of 4 mM ATP (FIGS. 3A and 3B) or in the presence of 0.1 mM ATP.

The average number of revolutions in the presence of 4 mM ATP was about 2.6 rps (revolutions per sec) or fewer. The average number of revolutions in the presence of 1 mM ATP was about 2.4 rps or fewer. Assuming that one revolution consumes three molecules of ATP, the revolution speed is in good agreement with the ATP hydrolysis speed observed in the bulk enzyme reaction theory (hydrolysis of about 10 ATPs per sec). Also, at 0.5 mM ATP the average number of revolutions is decreased to about 2.2 rps (FIG. 3C).

2-3. Rotation of F Subunit

Figure 4:
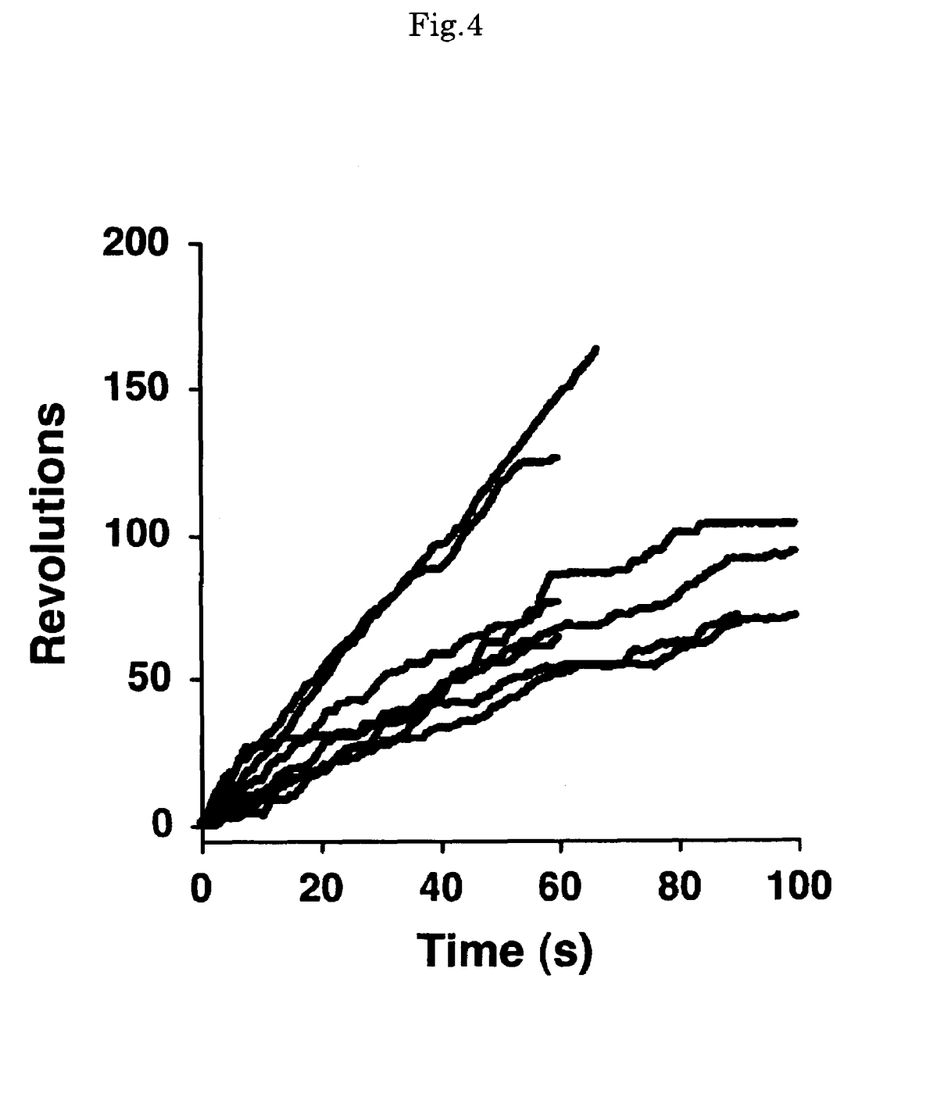
FIG. 4 indicates the measurements of rotation of bead fixed on an F subunit in 4 mM ATP solution.

The rotation of a bead bound to F subunit was observed as well. Under a condition of 4 mM ATP concentration, 1 to 3 rotating beads were observed (FIG. 4). The rotation direction was always counterclockwise. The revolution speed was about 2.5 rps, which was almost the same as the revolution speed of the bead on D subunit.

INDUSTRIAL APPLICABILITY

As described in detail thus far, the invention of this filing provides $V_1$-ATPase as a novel rotary motor molecule. In addition, a variety of variant $V_1$-ATPases are provided which are more practical forms of this rotary motor molecule $V_1$-ATPase. These will greatly contribute to the fabrication of a micromachine, a nanomachine, and the like.

---

The invention claimed is:

1. A heat resistant $V_1$ATPase, which is a $V_1$ portion of a $V_0V_1$-ATPase derived from the thermophile bacteria, *Thermus thermophilus*, and is a complex molecule having three A subunits, three B subunits and one D subunit, wherein:
   the A and B subunits are arranged alternately to form a hexamer cylinder, and the D subunit is embedded in the central cavity of the cylinder,
   each A subunit has the amino acid sequence of SEQ ID NO: 3,
   each B subunit has the amino acid sequence of SEQ ID NO: 4 and the D subunit has the amino acid sequence of SEQ ID NO: 5,
   wherein, the A subunits have two substitutions: an Ala residue for the 232nd Ser residue and Ser residue for the 235th Thr residue in SEQ ID NO:3;

wherein, optionally the D subunit further comprises a joint material, and wherein, the joint material is optionally bound to at least one Cys residue substituted for the 48$^{th}$ Glu residue and Cys residue substituted for the 55$^{th}$ Gln residue in SEQ ID NO: 5.

2. The V$_1$-ATPase of claim 1, wherein at least one of the A subunit and the B subunit thereof is fixed on a substrate.

3. The V$_1$-ATPase of claim 2, which is fixed on the substrate via a His tag bound to the N terminal of the A subunit.

4. The V$_1$-ATPase of claim 1, wherein the D subunit further comprises a joint material.

5. The V$_1$-ATPase of claim 2, wherein the D subunit further comprises a joint material.

6. The V$_1$-ATPase of claim 3, wherein the D subunit further comprises a joint material.

7. The V$_1$-ATPase of claim 4, wherein the joint is bound to at least one of Cys residue substituted for the 48$^{th}$ Glu residue and Cys residue substituted for the 55$^{th}$ Gln residue in SEQ ID NO: 5.

8. The V$_1$-ATPase of claim 5, wherein the joint is bound to at least one of Cys residue substituted for the 48$^{th}$ Glu residue and Cys residue substituted for the 55$^{th}$ Gln residue in SEQ ID NO: 5.

9. The V$_1$-ATPase of claim 6, wherein the joint is bound to at least one of Cys residue substituted for the 48$^{th}$ Glu residue and Cys residue substituted for the 55$^{th}$ Gln residue in SEQ ID NO: 5.

10. The V$_1$-ATPase of claim 7, wherein all Cys residues in the A subunit and the B subunit are replaced by non-Cys residues.

11. The V$_1$-ATPase of claim 8, wherein all Cys residues in the A subunit and the B subunit are replaced by non-Cys residues.

12. The V$_1$-ATPase of claim 9, wherein all Cys residues in the A subunit and the B subunit are replaced by non-Cys residues.

* * * * *

SEQUENCE LISTING

```
<160> NUMBER OF SEQ ID NOS: 5

<210> SEQ ID NO 1
<211> LENGTH: 4199
<212> TYPE: DNA
<213> ORGANISM: Thermus thermophilus
<220> FEATURE:
<221> NAME/KEY: CDS
<222> LOCATION: (1)..(318)
<220> FEATURE:
<221> NAME/KEY: CDS
<222> LOCATION: (334)..(2067)
<220> FEATURE:
<221> NAME/KEY: CDS
<222> LOCATION: (2081)..(3514)
<220> FEATURE:
<221> NAME/KEY: CDS
<222> LOCATION: (3528)..(4196)

<400> SEQUENCE: 1 gtg agg atg gcg gtg atc gcc gat ccc gag acc gcc cag ggg ttc cgg        48
Val Arg Met Ala Val Ile Ala Asp Pro Glu Thr Ala Gln Gly Phe Arg
 1               5                  10                  15 ctc gcg ggc ctc gag ggc tac ggg gcc tct tcg gcg gag gag gcc caa        96
Leu Ala Gly Leu Glu Gly Tyr Gly Ala Ser Ser Ala Glu Glu Ala Gln
             20                  25                  30 agc ctc ctg gaa acc ctc gtg gag cgg ggc ggc tac gcc ctg gtg gcc       144
Ser Leu Leu Glu Thr Leu Val Glu Arg Gly Gly Tyr Ala Leu Val Ala
         35                  40                  45 gtg gac gag gcg ctc ctc ccc gac ccc gag cgg gcg gtg gag cgc ctc       192
Val Asp Glu Ala Leu Leu Pro Asp Pro Glu Arg Ala Val Glu Arg Leu
     50                  55                  60 atg cgg ggc agg gac ctc ccc gtg ctc ctg ccc atc gcg ggg ctg aag       240
Met Arg Gly Arg Asp Leu Pro Val Leu Leu Pro Ile Ala Gly Leu Lys
 65                  70                  75                  80 gag gcc ttc cag ggg cac gac gtg gaa ggc tac atg cgg gag ctg gtg       288
Glu Ala Phe Gln Gly His Asp Val Glu Gly Tyr Met Arg Glu Leu Val
                 85                  90                  95 agg aag acc atc ggc ttt gac atc aag ctg tagaatggag ggacg atg atc     339
Arg Lys Thr Ile Gly Phe Asp Ile Lys Leu                Met Ile
                100                 105
```

-continued

| | |
|---|---|
| caa ggg gtg atc cag aag atc gcg ggc ccg gcg gtg atc gcc aag ggc<br>Gln Gly Val Ile Gln Lys Ile Ala Gly Pro Ala Val Ile Ala Lys Gly<br>110               115                  120 | 387 |
| atg ctc ggg gcc cgc atg tac gac atc tgc aag gtg ggc gaa gag ggc<br>Met Leu Gly Ala Arg Met Tyr Asp Ile Cys Lys Val Gly Glu Glu Gly<br>125               130               135            140 | 435 |
| ctc gtg ggc gag atc atc cgc ctg gac ggg gac acg gcc ttc gtc cag<br>Leu Val Gly Glu Ile Ile Arg Leu Asp Gly Asp Thr Ala Phe Val Gln<br>145               150               155 | 483 |
| gtc tac gag gac acc tcg ggc cta aag gtg ggg gag ccc gtg gtc tcc<br>Val Tyr Glu Asp Thr Ser Gly Leu Lys Val Gly Glu Pro Val Val Ser<br>         160                 165            170 | 531 |
| acg ggg ctt ccc ttg gcg gtg gag ctc ggc ccc ggg atg ctg aac ggc<br>Thr Gly Leu Pro Leu Ala Val Glu Leu Gly Pro Gly Met Leu Asn Gly<br>175               180              185 | 579 |
| atc tac gac ggc atc cag cgc ccc ctg gag cgc atc cgg gag aag acg<br>Ile Tyr Asp Gly Ile Gln Arg Pro Leu Glu Arg Ile Arg Glu Lys Thr<br>190               195               200 | 627 |
| ggg atc tac atc acc cgg ggc gtg gtg gtc cac gcc ctg gac cgg gag<br>Gly Ile Tyr Ile Thr Arg Gly Val Val Val His Ala Leu Asp Arg Glu<br>205               210              215            220 | 675 |
| aag aag tgg gcc tgg acg ccc atg gtc aag ccc ggg gac gag gtg cgg<br>Lys Lys Trp Ala Trp Thr Pro Met Val Lys Pro Gly Asp Glu Val Arg<br>                225               230            235 | 723 |
| ggg ggt atg gtc ctg ggc acg gtg ccc gag ttc ggc ttc acc cac aag<br>Gly Gly Met Val Leu Gly Thr Val Pro Glu Phe Gly Phe Thr His Lys<br>         240                 245            250 | 771 |
| atc ctg gta ccc ccg gac gtg cgg ggc cgg gtc aag gag gtg aag ccc<br>Ile Leu Val Pro Pro Asp Val Arg Gly Arg Val Lys Glu Val Lys Pro<br>255               260              265 | 819 |
| gcc ggg gag tac acc gtg gag gag ccg gtg gtg gtc ctc gag gac ggc<br>Ala Gly Glu Tyr Thr Val Glu Glu Pro Val Val Val Leu Glu Asp Gly<br>270               275              280 | 867 |
| acc gag ctc aag atg tac cac acc tgg ccc gtt cgc cgg gcg agg ccc<br>Thr Glu Leu Lys Met Tyr His Thr Trp Pro Val Arg Arg Ala Arg Pro<br>285               290              295            300 | 915 |
| gtg caa agg aag ctt gac ccc aac acc ccc ttc ctc acg ggg atg cgc<br>Val Gln Arg Lys Leu Asp Pro Asn Thr Pro Phe Leu Thr Gly Met Arg<br>                305               310            315 | 963 |
| atc ctg gac gtc ctc ttc ccc gtg gcc atg ggg ggc acc gcc gcc atc<br>Ile Leu Asp Val Leu Phe Pro Val Ala Met Gly Gly Thr Ala Ala Ile<br>         320                 325            330 | 1011 |
| cct ggg ccc ttc ggc agc ggc aag acc gtg acc cag cag tcc ctg gcc<br>Pro Gly Pro Phe Gly Ser Gly Lys Thr Val Thr Gln Gln Ser Leu Ala<br>335               340              345 | 1059 |
| aag tgg tcc aac gcc gac gtg gtg gtc tac gtg ggc tgc ggg gag cgg<br>Lys Trp Ser Asn Ala Asp Val Val Val Tyr Val Gly Cys Gly Glu Arg<br>350               355              360 | 1107 |
| ggg aac gag atg acc gac gtg ctc gtg gag ttc ccc gag ctc acc gac<br>Gly Asn Glu Met Thr Asp Val Leu Val Glu Phe Pro Glu Leu Thr Asp<br>365               370              375            380 | 1155 |
| ccc aag acg ggg ggg ccc ttg atg cac cgc acc gtc ctc atc gcc aac<br>Pro Lys Thr Gly Gly Pro Leu Met His Arg Thr Val Leu Ile Ala Asn<br>                385               390            395 | 1203 |
| acc tcc aac atg ccc gtg gcc gcc cgc gag gcc agc atc tac gtg ggc<br>Thr Ser Asn Met Pro Val Ala Ala Arg Glu Ala Ser Ile Tyr Val Gly<br>         400                 405            410 | 1251 |
| gtg acc atc gcc gag tac ttc cgc gac cag ggc ttc tcc gtg gcc ctc<br>Val Thr Ile Ala Glu Tyr Phe Arg Asp Gln Gly Phe Ser Val Ala Leu | 1299 |

-continued

| | | |
|---|---|---|
| | 415 420 425 | |
| atg gcc gac tcc acg agc cgc tgg gcc gag gct ttg cgc gag atc tct<br>Met Ala Asp Ser Thr Ser Arg Trp Ala Glu Ala Leu Arg Glu Ile Ser<br>430 435 440 | 1347 |
| agc cgc ctc gag gag atg ccc gcc gag gag ggc tac ccg ccc tac ctc<br>Ser Arg Leu Glu Glu Met Pro Ala Glu Glu Gly Tyr Pro Pro Tyr Leu<br>445 450 455 460 | 1395 |
| gcc gcc agg ctc gcc gcc ttc tac gag cgg gcg ggc aag gtc atc acc<br>Ala Ala Arg Leu Ala Ala Phe Tyr Glu Arg Ala Gly Lys Val Ile Thr<br>465 470 475 | 1443 |
| ctg ggc ggc gag gag ggg gcg gtg acc atc gtg ggg gcc gtc tcc ccg<br>Leu Gly Gly Glu Glu Gly Ala Val Thr Ile Val Gly Ala Val Ser Pro<br>480 485 490 | 1491 |
| ccg ggc ggc gac atg tcc gag ccc gtg acc cag tcc acc ttg agg atc<br>Pro Gly Gly Asp Met Ser Glu Pro Val Thr Gln Ser Thr Leu Arg Ile<br>495 500 505 | 1539 |
| gtg ggg gcc ttc tgg cgg ctt gac gcc tcc ctg gcc ttc cgc cgc cac<br>Val Gly Ala Phe Trp Arg Leu Asp Ala Ser Leu Ala Phe Arg Arg His<br>510 515 520 | 1587 |
| ttc ccc gcc atc aac tgg aac ggc tcc tac agc ctc ttc acc tcc gcc<br>Phe Pro Ala Ile Asn Trp Asn Gly Ser Tyr Ser Leu Phe Thr Ser Ala<br>525 530 535 540 | 1635 |
| ctt gac ccc tgg tac cgg gag aac gtg gcc gag gac tac ccc gag ctc<br>Leu Asp Pro Trp Tyr Arg Glu Asn Val Ala Glu Asp Tyr Pro Glu Leu<br>545 550 555 | 1683 |
| cgc gac gcc atc tcc gag ctt ttg cag cgg gag gcg ggc ctc cag gag<br>Arg Asp Ala Ile Ser Glu Leu Leu Gln Arg Glu Ala Gly Leu Gln Glu<br>560 565 570 | 1731 |
| atc gtc cag ctc gtg ggg ccg gac gcc ctc cag gac gcc gag cgc ctc<br>Ile Val Gln Leu Val Gly Pro Asp Ala Leu Gln Asp Ala Glu Arg Leu<br>575 580 585 | 1779 |
| gtc att gag gtg ggc cgg atc atc cgc gag gac ttc ctg cag cag aac<br>Val Ile Glu Val Gly Arg Ile Ile Arg Glu Asp Phe Leu Gln Gln Asn<br>590 595 600 | 1827 |
| gcc tac cac gag gtg gac gcc tac tgc tcc atg aag aag gcc tac ggg<br>Ala Tyr His Glu Val Asp Ala Tyr Cys Ser Met Lys Lys Ala Tyr Gly<br>605 610 615 620 | 1875 |
| atc atg aag atg atc ctc gcc ttc tac aag gag gcg gag gcg gcc atc<br>Ile Met Lys Met Ile Leu Ala Phe Tyr Lys Glu Ala Glu Ala Ala Ile<br>625 630 635 | 1923 |
| aag cgg ggg gtt tcc ata gac gag atc ctg cag ctc ccc gtt ctg gag<br>Lys Arg Gly Val Ser Ile Asp Glu Ile Leu Gln Leu Pro Val Leu Glu<br>640 645 650 | 1971 |
| cgc atc ggc cgc gcc cgc tac gtg agc gag gag gag ttc ccc gcc tac<br>Arg Ile Gly Arg Ala Arg Tyr Val Ser Glu Glu Glu Phe Pro Ala Tyr<br>655 660 665 | 2019 |
| ttt gag gag gcc atg aag gag atc cag ggg gcc ttc aag gcc ctg gcc<br>Phe Glu Glu Ala Met Lys Glu Ile Gln Gly Ala Phe Lys Ala Leu Ala<br>670 675 680 | 2067 |
| taaaggggga gag atg gac ctt ctg aag aag gag tac acg ggc atc acc<br>Met Asp Leu Leu Lys Lys Glu Tyr Thr Gly Ile Thr<br>685 690 695 | 2116 |
| tac atc tcg ggg cct ctt ctc ttc gtg gag aac gcc aag gac ctg gcc<br>Tyr Ile Ser Gly Pro Leu Leu Phe Val Glu Asn Ala Lys Asp Leu Ala<br>700 705 710 | 2164 |
| tac ggg gcc atc gtg gac atc aag gac ggc acg ggc cgg gtc cgc ggc<br>Tyr Gly Ala Ile Val Asp Ile Lys Asp Gly Thr Gly Arg Val Arg Gly<br>715 720 725 | 2212 |

```
ggc cag gtg att gag gtc tcc gag gag tac gcc gtc atc cag gtg ttt         2260
Gly Gln Val Ile Glu Val Ser Glu Glu Tyr Ala Val Ile Gln Val Phe
        730             735                 740 gag gaa acc act ggg ctg gac ctg gcc acg acc agc gtg agc ctg gtg         2308
Glu Glu Thr Thr Gly Leu Asp Leu Ala Thr Thr Ser Val Ser Leu Val
745                 750                 755                 760 gag gac gtg gcc cgg ctt ggg gtc tcc aag gag atg ctg ggc cgc cgc         2356
Glu Asp Val Ala Arg Leu Gly Val Ser Lys Glu Met Leu Gly Arg Arg
                765                 770                 775 ttc aac ggc atc ggc aag ccc ata gac ggc ctg ccg ccc atc acc ccg         2404
Phe Asn Gly Ile Gly Lys Pro Ile Asp Gly Leu Pro Pro Ile Thr Pro
            780                 785                 790 gag aag cgg ctc ccc atc acc ggc ctt ccc tta aac ccc gtg gcc cgg         2452
Glu Lys Arg Leu Pro Ile Thr Gly Leu Pro Leu Asn Pro Val Ala Arg
        795                 800                 805 agg aag ccg gag cag ttc atc cag acg ggc atc tcc acc att gac gtg         2500
Arg Lys Pro Glu Gln Phe Ile Gln Thr Gly Ile Ser Thr Ile Asp Val
810                 815                 820 atg aac acc ctg gtc cgg ggg cag aag ctt ccc atc ttc tcc ggc tcg         2548
Met Asn Thr Leu Val Arg Gly Gln Lys Leu Pro Ile Phe Ser Gly Ser
825                 830                 835                 840 ggg ctt ccc gcc aac gag atc gcc gcc cag atc gcc cgc cag gcc acg         2596
Gly Leu Pro Ala Asn Glu Ile Ala Ala Gln Ile Ala Arg Gln Ala Thr
                845                 850                 855 gtg cgc ccc gac ctc tcc ggg gag ggg gag aag gag gag ccc ttc gcc         2644
Val Arg Pro Asp Leu Ser Gly Glu Gly Glu Lys Glu Glu Pro Phe Ala
            860                 865                 870 gtg gtc ttc gcc gcc atg ggg atc acg cag cgg gag ctc tcc tac ttc         2692
Val Val Phe Ala Ala Met Gly Ile Thr Gln Arg Glu Leu Ser Tyr Phe
        875                 880                 885 atc cag gag ttt gag cgc acc ggg gcc ctg agc cgc tcc gtc ctc ttc         2740
Ile Gln Glu Phe Glu Arg Thr Gly Ala Leu Ser Arg Ser Val Leu Phe
890                 895                 900 ctg aac aag gcg gac gac ccc acc att gag cgc atc ctc acc ccc cgc         2788
Leu Asn Lys Ala Asp Asp Pro Thr Ile Glu Arg Ile Leu Thr Pro Arg
905                 910                 915                 920 atg gcc ctc acc gtg gcc gag tac ctg gcc ttt gag cac gac tac cac         2836
Met Ala Leu Thr Val Ala Glu Tyr Leu Ala Phe Glu His Asp Tyr His
                925                 930                 935 gtc ctc gtc atc ctc acg gac atg acc aac tac tgc gag gcc ttg cgg         2884
Val Leu Val Ile Leu Thr Asp Met Thr Asn Tyr Cys Glu Ala Leu Arg
            940                 945                 950 gag atc ggg gcc gcc cgc gag gag atc ccg ggc cgc cgc ggt tac ccc         2932
Glu Ile Gly Ala Ala Arg Glu Glu Ile Pro Gly Arg Arg Gly Tyr Pro
        955                 960                 965 ggc tac atg tac acc gac ctg gcc acc atc tac gag cgc gcc ggg gtg         2980
Gly Tyr Met Tyr Thr Asp Leu Ala Thr Ile Tyr Glu Arg Ala Gly Val
970                 975                 980 gtg gag ggg aag aag ggg agc gtg acc cag atc ccc atc ctc tcc atg         3028
Val Glu Gly Lys Lys Gly Ser Val Thr Gln Ile Pro Ile Leu Ser Met
985                 990                 995                 1000 ccc gac gac gac cgc acc cac ccc atc ccc gac ctc acg ggc tac atc         3076
Pro Asp Asp Asp Arg Thr His Pro Ile Pro Asp Leu Thr Gly Tyr Ile
                1005                1010                1015 acc gag ggg cag atc cag ctc tcc cgg gag ctc cac cgc aag ggc atc         3124
Thr Glu Gly Gln Ile Gln Leu Ser Arg Glu Leu His Arg Lys Gly Ile
            1020                1025                1030 tac ccg ccc att gac ccc ttg ccc tcc ctc tcc cgg ctc atg aac aac         3172
Tyr Pro Pro Ile Asp Pro Leu Pro Ser Leu Ser Arg Leu Met Asn Asn
        1035                1040                1045
```

```
ggc gtg ggc aag ggc aag acc cgg gag gac cac aag cag gtc tcc gac    3220
Gly Val Gly Lys Gly Lys Thr Arg Glu Asp His Lys Gln Val Ser Asp
    1050                1055                1060 cag ctc tac tcc gcc tac gcc aac ggg gtg gac atc cgg aag ctc gtg    3268
Gln Leu Tyr Ser Ala Tyr Ala Asn Gly Val Asp Ile Arg Lys Leu Val
1065                1070                1075                1080 gcc atc atc ggc gag gac gcc ctc acg gag aac gac cgc cgt tac ctc    3316
Ala Ile Ile Gly Glu Asp Ala Leu Thr Glu Asn Asp Arg Arg Tyr Leu
            1085                1090                1095 cag ttc gcc gac gcc ttt gaa cgg ttc ttc atc aac cag ggg cag cag    3364
Gln Phe Ala Asp Ala Phe Glu Arg Phe Phe Ile Asn Gln Gly Gln Gln
        1100                1105                1110 aac cgc tcc att gag gag agc ctg cag atc gcc tgg gcc ctc ctc tcc    3412
Asn Arg Ser Ile Glu Glu Ser Leu Gln Ile Ala Trp Ala Leu Leu Ser
    1115                1120                1125 atg ctg ccc cag ggc gag ctc aag cgc atc tcc aag gac cac atc ggc    3460
Met Leu Pro Gln Gly Glu Leu Lys Arg Ile Ser Lys Asp His Ile Gly
1130                1135                1140 aag tac tac ggc cag aag ctg gag gag atc tgg ggc gcg ccc cag gcc    3508
Lys Tyr Tyr Gly Gln Lys Leu Glu Glu Ile Trp Gly Ala Pro Gln Ala
1145                1150                1155                1160 ctg gac taagggaggg tag atg agc cag gtg agc ccc acc cgg atg aac    3557
Leu Asp             Met Ser Gln Val Ser Pro Thr Arg Met Asn
                                1165                1170 ctt ctg cag agg cgg ggg cag ctc cgc ctg gcg cag aag ggg gtg gac    3605
Leu Leu Gln Arg Arg Gly Gln Leu Arg Leu Ala Gln Lys Gly Val Asp
    1175                1180                1185 ctc ctc aag aag aag cgg gac gcc ctg gtg gcc gag ttc ttc ggc ctg    3653
Leu Leu Lys Lys Lys Arg Asp Ala Leu Val Ala Glu Phe Phe Gly Leu
1190                1195                1200 gtg cgg gag gcc atg gag gcc agg aag gcc ctg gac cag gcg gcc aag    3701
Val Arg Glu Ala Met Glu Ala Arg Lys Ala Leu Asp Gln Ala Ala Lys
1205                1210                1215                1220 gag gcc tac gcc gcc ctc ctc ctg gcc cag gcc ttt gac ggg ccg gag    3749
Glu Ala Tyr Ala Ala Leu Leu Leu Ala Gln Ala Phe Asp Gly Pro Glu
        1225                1230                1235 gtg gtg gcg ggg gcg gcc ctt ggg gtc ccg ccc ctc gag ggg gtg gag    3797
Val Val Ala Gly Ala Ala Leu Gly Val Pro Pro Leu Glu Gly Val Glu
            1240                1245                1250 gcg gag gtg gag aac gtc tgg ggg agc aag gtg ccg agg ctc aag gcc    3845
Ala Glu Val Glu Asn Val Trp Gly Ser Lys Val Pro Arg Leu Lys Ala
1255                1260                1265 acc ttc ccc gac ggg gcc ctc ctt tcc ccg gtg ggg acc ccg gcc tac    3893
Thr Phe Pro Asp Gly Ala Leu Leu Ser Pro Val Gly Thr Pro Ala Tyr
    1270                1275                1280 acc ctc gag gcc agc cgg gcc ttc cgc cgc tac gcc gag gcc ctg atc    3941
Thr Leu Glu Ala Ser Arg Ala Phe Arg Arg Tyr Ala Glu Ala Leu Ile
1285                1290                1295                1300 cgg gtg gcc aac acc gag acc cgc ctg aag aag atc ggg gag gag atc    3989
Arg Val Ala Asn Thr Glu Thr Arg Leu Lys Lys Ile Gly Glu Glu Ile
        1305                1310                1315 aag aag acc acg cgg cgg gtg aac gcc ctg gag cag gtg gtg atc ccg    4037
Lys Lys Thr Thr Arg Arg Val Asn Ala Leu Glu Gln Val Val Ile Pro
            1320                1325                1330 ggg atc cgc gcc cag atc cgc ttc atc cag cag gtc ctg gag cag cgg    4085
Gly Ile Arg Ala Gln Ile Arg Phe Ile Gln Gln Val Leu Glu Gln Arg
1335                1340                1345 gaa cgg gag gac acc ttc cgc ctc aag cgc atc aag ggc aag att gag    4133
Glu Arg Glu Asp Thr Phe Arg Leu Lys Arg Ile Lys Gly Lys Ile Glu
```

-continued

```
              1350                1355                1360
gcc cgg gag gcc gag gag gag ggc ggc cgg ccc aac ccg cag gtg gag      4181
Ala Arg Glu Ala Glu Glu Glu Gly Gly Arg Pro Asn Pro Gln Val Glu
1365                1370                1375                1380 atc ggg gcg ggc ctt taa                                              4199
Ile Gly Ala Gly Leu
              1385
```

<210> SEQ ID NO 2
<211> LENGTH: 106
<212> TYPE: PRT
<213> ORGANISM: Thermus thermophilus

<400> SEQUENCE: 2

```
Val Arg Met Ala Val Ile Ala Asp Pro Glu Thr Ala Gln Gly Phe Arg
 1               5                  10                  15

Leu Ala Gly Leu Glu Gly Tyr Gly Ala Ser Ser Ala Glu Glu Ala Gln
             20                  25                  30

Ser Leu Leu Glu Thr Leu Val Glu Arg Gly Gly Tyr Ala Leu Val Ala
         35                  40                  45

Val Asp Glu Ala Leu Leu Pro Asp Pro Glu Arg Ala Val Glu Arg Leu
     50                  55                  60

Met Arg Gly Arg Asp Leu Pro Val Leu Leu Pro Ile Ala Gly Leu Lys
 65                  70                  75                  80

Glu Ala Phe Gln Gly His Asp Val Gly Tyr Met Arg Glu Leu Val
                 85                  90                  95

Arg Lys Thr Ile Gly Phe Asp Ile Lys Leu
            100                 105
```

<210> SEQ ID NO 3
<211> LENGTH: 578
<212> TYPE: PRT
<213> ORGANISM: Thermus thermophilus

<400> SEQUENCE: 3

```
Met Ile Gln Gly Val Ile Gln Lys Ile Ala Gly Pro Ala Val Ile Ala
 1               5                  10                  15

Lys Gly Met Leu Gly Ala Arg Met Tyr Asp Ile Cys Lys Val Gly Glu
             20                  25                  30

Glu Gly Leu Val Gly Glu Ile Ile Arg Leu Asp Gly Asp Thr Ala Phe
         35                  40                  45

Val Gln Val Tyr Glu Asp Thr Ser Gly Leu Lys Val Gly Glu Pro Val
     50                  55                  60

Val Ser Thr Gly Leu Pro Leu Ala Val Glu Leu Gly Pro Gly Met Leu
 65                  70                  75                  80

Asn Gly Ile Tyr Asp Gly Ile Gln Arg Pro Leu Glu Arg Ile Arg Glu
                 85                  90                  95

Lys Thr Gly Ile Tyr Ile Thr Arg Gly Val Val His Ala Leu Asp
            100                 105                 110

Arg Glu Lys Lys Trp Ala Trp Thr Pro Met Val Lys Pro Gly Asp Glu
        115                 120                 125

Val Arg Gly Gly Met Val Leu Gly Thr Val Pro Glu Phe Gly Phe Thr
    130                 135                 140

His Lys Ile Leu Val Pro Pro Asp Val Arg Gly Arg Val Lys Glu Val
145                 150                 155                 160

Lys Pro Ala Gly Glu Tyr Thr Val Glu Glu Pro Val Val Leu Glu
                165                 170                 175
```

```
Asp Gly Thr Glu Leu Lys Met Tyr His Thr Trp Pro Val Arg Arg Ala
            180                 185                 190

Arg Pro Val Gln Arg Lys Leu Asp Pro Asn Thr Pro Phe Leu Thr Gly
            195                 200                 205

Met Arg Ile Leu Asp Val Leu Phe Pro Val Ala Met Gly Gly Thr Ala
            210                 215                 220

Ala Ile Pro Gly Pro Phe Gly Ser Gly Lys Thr Val Thr Gln Gln Ser
225                 230                 235                 240

Leu Ala Lys Trp Ser Asn Ala Asp Val Val Tyr Val Gly Cys Gly
            245                 250                 255

Glu Arg Gly Asn Glu Met Thr Asp Val Leu Val Glu Phe Pro Glu Leu
            260                 265                 270

Thr Asp Pro Lys Thr Gly Gly Pro Leu Met His Arg Thr Val Leu Ile
            275                 280                 285

Ala Asn Thr Ser Asn Met Pro Val Ala Ala Arg Glu Ala Ser Ile Tyr
            290                 295                 300

Val Gly Val Thr Ile Ala Glu Tyr Phe Arg Asp Gln Gly Phe Ser Val
305                 310                 315                 320

Ala Leu Met Ala Asp Ser Thr Ser Arg Trp Ala Glu Ala Leu Arg Glu
            325                 330                 335

Ile Ser Ser Arg Leu Glu Glu Met Pro Ala Glu Gly Tyr Pro Pro
            340                 345                 350

Tyr Leu Ala Ala Arg Leu Ala Ala Phe Tyr Glu Arg Ala Gly Lys Val
            355                 360                 365

Ile Thr Leu Gly Gly Glu Gly Ala Val Thr Ile Val Gly Ala Val
            370                 375                 380

Ser Pro Pro Gly Gly Asp Met Ser Glu Pro Val Thr Gln Ser Thr Leu
385                 390                 395                 400

Arg Ile Val Gly Ala Phe Trp Arg Leu Asp Ala Ser Leu Ala Phe Arg
            405                 410                 415

Arg His Phe Pro Ala Ile Asn Trp Asn Gly Ser Tyr Ser Leu Phe Thr
            420                 425                 430

Ser Ala Leu Asp Pro Trp Tyr Arg Glu Asn Val Ala Glu Asp Tyr Pro
            435                 440                 445

Glu Leu Arg Asp Ala Ile Ser Glu Leu Leu Gln Arg Glu Ala Gly Leu
            450                 455                 460

Gln Glu Ile Val Gln Leu Val Gly Pro Asp Ala Leu Gln Asp Ala Glu
465                 470                 475                 480

Arg Leu Val Ile Glu Val Gly Arg Ile Ile Arg Glu Asp Phe Leu Gln
            485                 490                 495

Gln Asn Ala Tyr His Glu Val Asp Ala Tyr Cys Ser Met Lys Lys Ala
            500                 505                 510

Tyr Gly Ile Met Lys Met Ile Leu Ala Phe Tyr Lys Glu Ala Glu Ala
            515                 520                 525

Ala Ile Lys Arg Gly Val Ser Ile Asp Glu Ile Leu Gln Leu Pro Val
            530                 535                 540

Leu Glu Arg Ile Gly Arg Ala Arg Tyr Val Ser Glu Glu Phe Pro
545                 550                 555                 560

Ala Tyr Phe Glu Glu Ala Met Lys Glu Ile Gln Gly Ala Phe Lys Ala
            565                 570                 575

Leu Ala
```

```
<210> SEQ ID NO 4
<211> LENGTH: 478
<212> TYPE: PRT
<213> ORGANISM: Thermus thermophilus

<400> SEQUENCE: 4

Met Asp Leu Leu Lys Lys Glu Tyr Thr Gly Ile Thr Tyr Ile Ser Gly
  1               5                  10                  15

Pro Leu Phe Val Glu Asn Ala Lys Asp Leu Ala Tyr Gly Ala Ile
             20                  25                  30

Val Asp Ile Lys Asp Gly Thr Gly Arg Val Arg Gly Gly Gln Val Ile
         35                  40                  45

Glu Val Ser Glu Glu Tyr Ala Val Ile Gln Val Phe Glu Glu Thr Thr
     50                  55                  60

Gly Leu Asp Leu Ala Thr Thr Ser Val Ser Leu Val Glu Asp Val Ala
 65                  70                  75                  80

Arg Leu Gly Val Ser Lys Glu Met Leu Gly Arg Arg Phe Asn Gly Ile
                 85                  90                  95

Gly Lys Pro Ile Asp Gly Leu Pro Pro Ile Thr Pro Glu Lys Arg Leu
            100                 105                 110

Pro Ile Thr Gly Leu Pro Leu Asn Pro Val Ala Arg Lys Pro Glu
        115                 120                 125

Gln Phe Ile Gln Thr Gly Ile Ser Thr Ile Asp Val Met Asn Thr Leu
    130                 135                 140

Val Arg Gly Gln Lys Leu Pro Ile Phe Ser Gly Ser Gly Leu Pro Ala
145                 150                 155                 160

Asn Glu Ile Ala Ala Gln Ile Ala Arg Gln Ala Thr Val Arg Pro Asp
                165                 170                 175

Leu Ser Gly Glu Gly Glu Lys Glu Glu Pro Phe Ala Val Val Phe Ala
            180                 185                 190

Ala Met Gly Ile Thr Gln Arg Glu Leu Ser Tyr Phe Ile Gln Glu Phe
        195                 200                 205

Glu Arg Thr Gly Ala Leu Ser Arg Ser Val Leu Phe Leu Asn Lys Ala
    210                 215                 220

Asp Asp Pro Thr Ile Glu Arg Ile Leu Thr Pro Arg Met Ala Leu Thr
225                 230                 235                 240

Val Ala Glu Tyr Leu Ala Phe Glu His Asp Tyr His Val Leu Val Ile
                245                 250                 255

Leu Thr Asp Met Thr Asn Tyr Cys Glu Ala Leu Arg Glu Ile Gly Ala
            260                 265                 270

Ala Arg Glu Glu Ile Pro Gly Arg Arg Gly Tyr Pro Gly Tyr Met Tyr
        275                 280                 285

Thr Asp Leu Ala Thr Ile Tyr Glu Arg Ala Gly Val Val Glu Gly Lys
    290                 295                 300

Lys Gly Ser Val Thr Gln Ile Pro Ile Leu Ser Met Pro Asp Asp
305                 310                 315                 320

Arg Thr His Pro Ile Pro Asp Leu Thr Gly Tyr Ile Thr Glu Gly Gln
                325                 330                 335

Ile Gln Leu Ser Arg Glu Leu His Arg Lys Gly Ile Tyr Pro Pro Ile
            340                 345                 350

Asp Pro Leu Pro Ser Leu Ser Arg Leu Met Asn Asn Gly Val Gly Lys
        355                 360                 365

Gly Lys Thr Arg Glu Asp His Lys Gln Val Ser Asp Gln Leu Tyr Ser
    370                 375                 380
```

-continued

```
Ala Tyr Ala Asn Gly Val Asp Ile Arg Lys Leu Val Ala Ile Ile Gly
385                 390                 395                 400

Glu Asp Ala Leu Thr Glu Asn Asp Arg Arg Tyr Leu Gln Phe Ala Asp
                405                 410                 415

Ala Phe Glu Arg Phe Phe Ile Asn Gln Gly Gln Asn Arg Ser Ile
            420                 425                 430

Glu Glu Ser Leu Gln Ile Ala Trp Ala Leu Leu Ser Met Leu Pro Gln
            435                 440                 445

Gly Glu Leu Lys Arg Ile Ser Lys Asp His Ile Gly Lys Tyr Tyr Gly
        450                 455                 460

Gln Lys Leu Glu Glu Ile Trp Gly Ala Pro Gln Ala Leu Asp
465                 470                 475

<210> SEQ ID NO 5
<211> LENGTH: 223
<212> TYPE: PRT
<213> ORGANISM: Thermus thermophilus

<400> SEQUENCE: 5

Met Ser Gln Val Ser Pro Thr Arg Met Asn Leu Leu Gln Arg Arg Gly
1               5                   10                  15

Gln Leu Arg Leu Ala Gln Lys Gly Val Asp Leu Leu Lys Lys Lys Arg
            20                  25                  30

Asp Ala Leu Val Ala Glu Phe Phe Gly Leu Val Arg Glu Ala Met Glu
        35                  40                  45

Ala Arg Lys Ala Leu Asp Gln Ala Ala Lys Glu Ala Tyr Ala Ala Leu
    50                  55                  60

Leu Leu Ala Gln Ala Phe Asp Gly Pro Glu Val Val Ala Gly Ala Ala
65                  70                  75                  80

Leu Gly Val Pro Pro Leu Glu Gly Val Glu Ala Glu Val Glu Asn Val
                85                  90                  95

Trp Gly Ser Lys Val Pro Arg Leu Lys Ala Thr Phe Pro Asp Gly Ala
            100                 105                 110

Leu Leu Ser Pro Val Gly Thr Pro Ala Tyr Thr Leu Glu Ala Ser Arg
            115                 120                 125

Ala Phe Arg Arg Tyr Ala Glu Ala Leu Ile Arg Val Ala Asn Thr Glu
130                 135                 140

Thr Arg Leu Lys Lys Ile Gly Glu Glu Ile Lys Lys Thr Thr Arg Arg
145                 150                 155                 160

Val Asn Ala Leu Glu Gln Val Val Ile Pro Gly Ile Arg Ala Gln Ile
                165                 170                 175

Arg Phe Ile Gln Gln Val Leu Gly Gln Arg Glu Arg Glu Asp Thr Phe
            180                 185                 190

Arg Leu Lys Arg Ile Lys Gly Lys Ile Glu Ala Arg Glu Ala Glu Glu
        195                 200                 205

Glu Gly Gly Arg Pro Asn Pro Gln Val Glu Ile Gly Ala Gly Leu
    210                 215                 220
```